United States Patent [19]

Dürr

[11] 4,431,439
[45] Feb. 14, 1984

[54] HERBICIDALLY ACTIVE 2-NITROPHENOXYPHENYLOXAZINES AND DIHYDROOXAZINES

[75] Inventor: Dieter Dürr, Bottmingen, Switzerland

[73] Assignee: Ciba-Geigy Corporation, Ardsley, N.Y.

[21] Appl. No.: 395,770

[22] Filed: Jul. 6, 1982

Related U.S. Application Data

[62] Division of Ser. No. 239,721, Mar. 2, 1981, Pat. No. 4,350,519.

[30] Foreign Application Priority Data

Mar. 5, 1980 [CH] Switzerland ............... 1739/80

[51] Int. Cl.³ ............... A01N 43/86; C07D 265/06; C07D 265/08
[52] U.S. Cl. ............... 71/88; 544/88
[58] Field of Search ............... 544/88; 71/88

[56] References Cited

U.S. PATENT DOCUMENTS 3,652,645 3/1972 Theissen ............... 71/115 X
3,928,416 12/1975 Bayer et al. ............... 71/116 X

FOREIGN PATENT DOCUMENTS 2261918 6/1973 Fed. Rep. of Germany.

Primary Examiner—Richard Raymond
Attorney, Agent, or Firm—Frederick H. Rabin

[57] ABSTRACT

Novel 2-nitro-5-phenoxyphenyloxazoles, -oxazines and -thiazoles are disclosed. These compounds have the formula

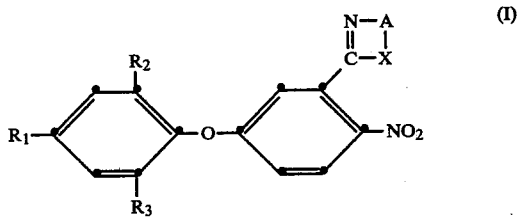

wherein A is a $C_2$–$C_3$alkylene or $C_2$–$C_3$alkenylene radical which can be substituted by $C_1$–$C_4$alkyl or $C_1$–$C_4$haloalkyl, each of $R_1$, $R_2$ and $R_3$ independently is hydrogen, halogen, trifluoromethyl, nitro or cyano, and X is oxygen, sulfur or an imino group. The novel compounds have herbicidal and plant growth-inhibiting properties. They are especially suitable for use as selective herbicides in crops of cereals.

9 Claims, No Drawings

HERBICIDALLY ACTIVE 2-NITROPHENOXYPHENYLOXAZINES AND DIHYDROOXAZINES

This is a division of application Ser. No. 239,721 filed on Mar. 2, 1981, now U.S. Pat. No. 4,350,519.

The present invention relates to novel herbicidally active 2-nitro-5-phenoxyphenyloxazoles, -oxazolines, -oxazines, -imidazoles, -pyrimidines and -thiazoles, to the production thereof, to compositions containing them, and to methods of selectively controlling weeds in crops of cultivated plants which comprises the use thereof.

Herbicidal 2-nitro-5-phenoxybenzoic acid derivatives are known e.g. from U.S. Pat. No. 3,928,416. The compounds of the present invention are novel and have good selective herbicidal action in cereals.

The 2-nitro-5-phenoxyphenyloxazoles, -oxazines, -imidazoles, -pyrimidines and -thiazoles of this invention have the formula I

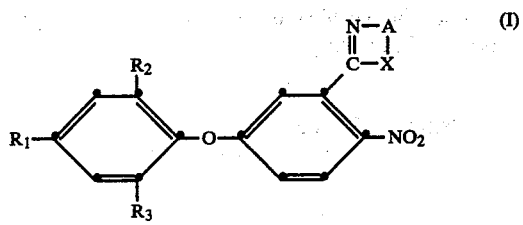

wherein A is a $C_2-C_3$alkylene or $C_2-C_3$alkenylene radical which can be substituted by $C_1-C_4$alkyl or $C_1-C_4$ haloalkyl, each of $R_1$, $R_2$ and $R_3$ independently is hydrogen, halogen, trifluoromethyl, nitro or cyano, and X is oxygen, sulfur, the imino group —NH— or a $C_1-C_4$alkylimino group >N-alkyl.

In the above definitions, the alkyl radicals can be straight-chain or branched. Halogen denotes fluorine, chlorine, bromine or iodine, with chlorine or bromine being preferred.

The compounds of the formula I are prepared by different methods which are known per se.

In a first process, the 2-nitro-5-phenoxyphenyloxazoles, -oxazines, -imidazoles, -pyrimidines and -thiazoles of the formula I are obtained by cyclising a 2-nitro-5-phenoxybenzoic or -thiobenzoic acid haloakylamide of the formula II

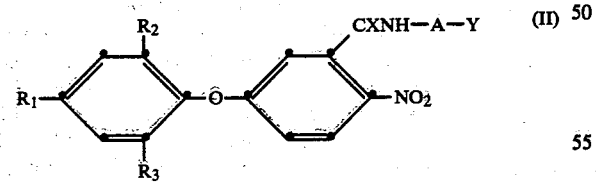

wherein A, $R_1$, $R_2$, $R_3$ and X are as defined for formula I, and Y is the OH group, a halogen atom or a sulfonic acid ester radical, in a solvent.

Suitable solvents for the above reaction are, in particular, water-soluble solvents, e.g. low molecular alcohols, ketones, dimethyl formamide, dimethyl sulfoxide, and also water-insoluble chlorinated hydrocarbons, ethers, and aromatic hydrocarbons.

The cyclisation reaction is conducted in the presence of a base, e.g. an alkali metal hydroxide or a quaternary ammonium hydroxide, if Y is a halogen atom or a sulfonic acid ester radical, but under acid conditions, e.g. in the presence of sulfuric acid, if Y is the hydroxyl group.

A suitable catalyst for the cyclisation is an alkali metal salt or a tertiary ammonium salt of a halide or a sulfonic acid.

The cyclisation reaction is carried out at room temperature, but to accelerate the process the reaction mixture can be heated to the boil. Reference is made in this connection e.g. to Synthesis 1980, page 63. The imidazole and pyrimidine compounds of the formula I are obtained by reacting a 1-cyano-2-nitro-5-phenoxybenzene of the formula III

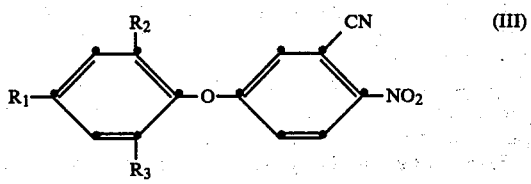

wherein $R_1$, $R_2$ and $R_3$ are as defined for formula I, in the presence of an excess of an alkylenediamine of the formula IV $$R_4—NH—A—NH_2 \qquad (IV)$$

wherein $R_4$ is hydrogen or $C_1-C_4$alkyl and A is as defined for formula I, in a pressure vessel, at elevated temperature, until ring closure has been effected. This method is also described e.g. in German Offenlegungsschrift No. 2 830 141.

The starting materials of the formula I can be prepared starting from known 2-nitro-5-phenoxybenzoic acids. Treatment of these acids with a halogenating agent, such as thionyl chloride, thionyl bromide, phosphoroxy chloride or bromide, gives the corresponding acid halide, which is then condensed with an alkanolamine in accordance with the reaction scheme:

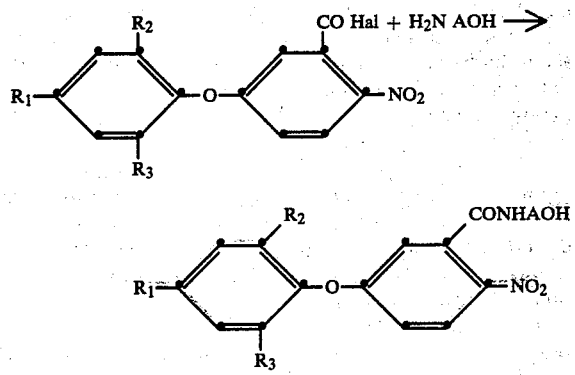

In the above formulae, A, $R_1$, $R_2$ and $R_3$ have the given meanings. The resultant 2-nitro-5-phenoxybenzalkanolamide is also treated with a halogenating agent, for example one of those referred to above, and reacted to give the haloalkylamide of the formula II.

The starting materials of the formula III are known (q.v. U.S. Pat. No. 3,928,416) or they can be obtained in a manner known per se by condensing a suitably substituted halobenzene and phenol in the presence of an acid acceptor.

Suitable alkyldiamines are, in particular, ethylenediamine, 1,2- and 1,3-propylenediamine, 1,2-, 2,3- and 1,3-butylenediamine.

The compounds of the formula I have good herbicidal properties. In high rates of application they can be used as total herbicides. However, it is more advantageous to use them in rates of application of about 0.1 to 5 kg per hectare as selective herbicides in crops of cultivated plants, either postemergence in germinating plants or preemergence in freshly sown ones. They inhibit or binder the occurrence of dicot weeds, but especially of monocot species such as *Lolium Alopecuris, Rottboellia, Sorghum, Digitaria, Setaria* and *Panicum*. Cultivated plants such as cereals, barley, wheat, rye, maize or rice, and also cotton and soybeans, are wholly unharmed, or at least unharmed at a rate of application of 1 kg/ha.

Some of the novel compounds are also suitable for the desiccation and defoliation of cotton and potato plants shortly before harvesting.

Depending on the activity of the respective compound, the nature of the soil, climatic and weather conditions, the nature and time of application, and the type of crop and species of weed to be controlled, the normal rates of application in which the herbicides of this invention are employed vary from 0.1 to 10 kg/ha, with the preferred range being from 0.5 to 4 kg.

The compounds of formula I also have good growth-regulating action (growth inhibition). In particular, they inhibit plant growth. The following effects may be cited as examples of the useful application of the compounds of the invention:

the reduction of the vegetative growth of soybeans and similar leguminous plants, resulting in an increase in yield of these crops;

the inhibition of the growth of grass, with the aim of reducing cutting work;

the inhibition of the vegetative growth of cereals, resulting in plants with shorter and sturdy stalks which are not so easily lodged by the action of wind and rain.

The compounds of the formula I all have good activity. The best results are obtained with compounds in which X is oxygen, and especially with those in which $R_1$ is hydrogen or halogen, $R_2$ is trifluoromethyl or halogen, $R_3$ is hydrogen, A is an ethylene, vinylene or propylene group which can be substituted by methyl or halomethyl, and X is oxygen.

The compounds of the formula I are stable compounds which are soluble in customary organic solvents such as alcohols, ethers, ketones, dimethyl formamide, dimethyl sulfoxide etc. They are not explosive or corrosive, and no special precautionary measures are required for handling them.

The compositions of the present invention are obtained in known manner by intimately mixing and grinding active ingredients (compounds) of the formula I with suitable carriers and/or adjuvants, if desired or necessary with the addition of antifoams, wetting agents, dispersants and/or solvents which are inert to the active ingredients. The active ingredients can be processed to the following formulations:

solid formulations: dusts, tracking powders, granules (coated granules, impregnated granules and homogenous granules), active ingredient concentrates which are dispersible in water: wettable powders, pastes, emulsions, emulsifiable concentrates, liquid formulations: solutions, dispersions.

The concentrations of active ingredient in the compositions of this invention are between 1 and 80 percent by weight. As circumstances may require, the active ingredients can also be applied in low concentrations of about 0.05 to 1 percent by weight.

The compositions of the present invention can be mixed with other biocidal compounds or compositions. Thus in addition to containing the compounds of the formula I, the compositions of the invention can also contain e.g. insecticides, fungicides, bactericides, fungistatic agents, bacteriostatic agents, nematocides or further herbicides, in order to broaden the activity spectrum.

The following Example illustrates the preparation of a 2-(2'-nitro-5'-phenoxyphenyl)-2-oxazoline of the formula I. Further compounds obtained in similar manner are listed in the subsequent table. Parts and percentages are by weight and pressures are in millibars. Further Examples describe the preparation of technical formulations containing the novel compounds of the formula I and also the herbicidal and plant growth-regulating action of these compounds.

EXAMPLE 1

2-[2'-Nitro-5'-(2"-chloro-4"-trifluoromethylphenoxy)-phenyl]-2-oxazoline

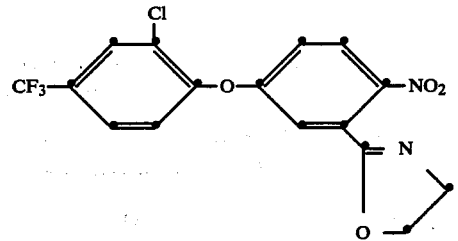

(a) A solution of 184 g (0.5 mole) of 2-nitro-5-(2'-chloro-4'-trifluoromethylphenoxy)benzoyl chloride in 500 ml of toluene is added dropwise at 20°–40° C. to a solution of 90 g of ethanolamine in 300 ml of dioxane. After 3 hours, 2-nitro-5-(2'-chloro-4'-trifluoromethylphenoxy)benzoic acid β-hydroxyethylamide is precipitated by addition of ice-water. The precipitate is dried, affording 199 g (98% of theory) of compound with a melting point of 142°–143° C.

(b) 199 g of this hydroxyethylamide are stirred with 150 g of thionyl chloride and 400 ml of toluene and the reaction mixture is kept at 40° C. for 20 hours. The reaction solution is then concentrated in vacuo. The residue is stirred in 500 ml of methylene chloride and 0.6 g of tetrabutylammonium chloride and then 42 g of powdered sodium hydroxide are added. The mixture is refluxed for 30 minutes and stirred for 10 hours. For working up the mixture is poured into water and the organic phase is separated, washed, dried and evaporated to dryness, leaving as residue the title compound in the form of a clear, viscous oil with a refractive index of $n_D^{25}$ 1.5703. Yield: 109 g (79% of theory).

Analysis: $C_{calc.}$ 49.70%, $H_{calc.}$ 2.61%, $N_{calc.}$ 7.24%; $C_{found}$ 49.5%, $H_{found}$ 2.6%, $N_{found}$ 7.1%.

Molecular weight: 346.71. The NMR spectrum is in accord with the structure.

The following compounds are prepared in analogous manner:

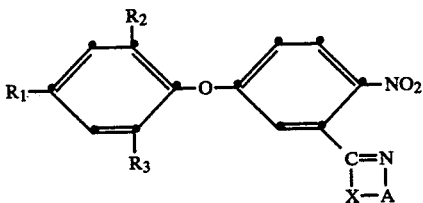

| No. | $R_1$ | $R_2$ | $R_3$ | $\overset{X-A}{\underset{-C=N}{\vert\phantom{x}\vert}}$ | physical data | (°C.) |
|---|---|---|---|---|---|---|
| 1 | $CF_3$ | Cl | H | 2-oxazolin-2-yl | $n_D^{25}$ | 1.5703 |
| 2 | $CF_3$ | Cl | H | 5-methyl-2-oxazolin-2-yl | $n_D^{25}$ | 1.5495 |
| 3 | $CF_3$ | Cl | H | 5,6-dihydro-4H-1,3-oxazin-2-yl | m.p. | 84° |
| 4 | $CF_3$ | Cl | H | 4,4-dimethyl-2-oxazolin-2-yl | $n_D^{27}$ | 1.5458 |
| 5 | $CF_3$ | Cl | H | 4-methyl-4-chloromethyl-2-oxazolin-2-yl | $n_D^{27}$ | 1.5490 |
| 6 | $CF_3$ | Cl | H | 5-methyl-oxazol-2-yl | $n_D^{26}$ | 1.5725 |
| 7 | $CF_3$ | Cl | H | 4-ethyl-2-oxazolin-2-yl | $n_D^{22}$ | 1.5505 |
| 8 | $CF_3$ | Cl | H | 4-methyl-2-oxazolin-2-yl | m.p. | 65–67° |
| 9 | $CF_3$ | Cl | Cl | 2-oxazolin-2-yl | m.p. | 118–122° |
| 10 | Cl | Cl | H | 2-oxazolin-2-yl | | |
| 11 | Cl | Cl | H | 4,4-dimethyl-2-oxazolin-2-yl | | |
| 12 | Br | Br | H | 2-oxazolin-2-yl | | |
| 13 | $CF_3$ | CN | H | 2-oxazolin-2-yl | | |
| 14 | Cl | CN | H | 5,6-dihydro-4H-1,3-oxazin-2-yl | | |
| 15 | $CF_3$ | $NO_2$ | H | 2-oxazolin-2-yl | | |
| 16 | Cl | $NO_2$ | H | 2-oxazolin-2-yl | | |
| 17 | Cl | Cl | Cl | 2-oxazolin-2-yl | | |
| 18 | Cl | $CF_3$ | H | 2-oxazolin-2-yl | | |
| 19 | $CF_3$ | Cl | H | 2-thiazolin-2-yl | m.p. | 140° |
| 20 | $CF_3$ | Cl | H | thiazol-2-yl | | |
| 21 | $CF_3$ | Cl | Cl | 2-thiazolin-2-yl | | |
| 22 | Cl | Cl | H | 2-thiazolin-2-yl | | |
| 23 | Cl | Cl | H | thiazol-2-yl | | |
| 24 | Cl | Cl | Cl | 2-thiazolin-2-yl | | |
| 25 | $CF_3$ | Cl | H | 5,6-dihydro-4H-pyrimidin-2-yl | | |
| 26 | $CF_3$ | Cl | H | 1-methyl-2-imidazolin-2-yl | | |
| 27 | $CF_3$ | Cl | H | imidazol-2-yl | | |

EXAMPLE 2

The compounds of the formula I can be processed to formulations suitable for use in agriculture by, for example, one of the following procedures:

Granules

The following substances are used to formulate 5% granules:
5 parts of 2-[2'-nitro-5'-(2''-chloro-4''-trifluoromethylphenoxy)-phenyl]-2-oxazoline,
0.25 part of epoxidised vegetable oil,
0.25 part of cetyl polyglycol ether,
3.50 parts of polyethylene glycol,
91 parts of kaolin (particle size 0.3–0.8 mm).

The active ingredient is mixed with the vegetable oil and the mixture is dissolved in 6 parts of acetone; the polyethylene glycol and cetyl polyglycol ether are then added. The resultant solution is sprayed on kaolin, and the acetone is subsequently evaporated in vacuo.

Wettable Powder

The following constituents are used to formulate (a) a 70% and (b) a 10% wettable powder:
(a) 70 parts of 2-[2'-nitro-5'-(2''-chloro-4''-trifluoromethylphenoxy)phenyl]-2-oxazoline,
5 parts of sodium dibutylnaphthylsulfate,
3 parts of naphthalenesulfonic acid/phenolsulfonic acid/formaldehyde condensate (3:2:1),
10 parts of kaolin,
12 parts of Champagne chalk;

(b) 10 parts of the above compound,
3 parts of a mixture of the sodium salts of saturated fatty alcohol sulfates,
5 parts of naphthalenesulfonic acid/formaldehyde condensate,
82 parts of kaolin.

The active ingredient is applied to the corresponding carriers (kaolin and chalk) and then these are mixed and ground, to yield wettable powders of excellent wettability and suspension power. By diluting these wettable powders with water it is possible to obtain suspensions containing 0.1 to 8% of active ingredient. These suspensions are suitable for controlling weeds in cultivations of plants.

Emulsifiable concentrate

The following ingredients are mixed to formulate a 25% emulsifiable concentrate:
25 parts of 2-[2'-nitro-5'-(2''-chloro-4''-trifluoromethylphenoxy)phenyl]-2-oxazoline,
5 parts of a mixture of nonylphenolpolyoxyethylene and calcium dodecylbenzenesulfonate,
15 parts of cyclohexanone,
55 parts of xylene.

This concentrate can be diluted with water to give emulsions in suitable concentrations of e.g. 0.1 to 10%. Such emulsions are suitable for controlling weeds in cultivated plants.

Paste

The following substances are used to formulate a 45% paste:

(a) 45 parts of 2-[2'-nitro-5'-(2"-chloro-4"-trifluoromethylphenoxy)phenyl]-2-oxazoline
5 parts of sodium aluminium silicate,
14 parts of cetyl polyglycol ether with 8 moles of ethylene oxide,
3 parts of oleyl polyglycol ether with 5 moles of ethylene oxide,
2 parts of spindle oil,
10 parts of polyethylene glycol,
23 parts of water.

(b) 45 parts of 2-[2'-nitro-5'-(2"-chloro-4"-trifluoromethylphenoxy)phenyl]-2-oxazoline,
5 parts of ethylene glycol,
3 parts of octylphenoxy polyethylene glycol containing 9-10 moles of ethylene oxide per mole of octylphenol,
3 parts of a mixture of aromatic sulfonesulfonic acids, condensed with formaldehyde as ammonium salt,
1 part of silicone oil in form of a 75% emulsion,
0.1 part of a mixture of 1-(3-chloroallyl)-3,5,7-triazoazonium-adamantane chloride with sodium carbonate (chloride value at least 11.5%),
0.2 part of a biopolymeric thickener containing a maximum of 100 bacilli per gram,
42.7 parts of water The active ingredient is intimately mixed with the adjuvants in appropriate devices and ground. By diluting the resultant paste with water, it is possible to prepare suspensions of the desired concentration.

EXAMPLE 3

The following test methods were employed to determine the herbicidal and plant growth-inhibiting action of the compounds of formula I.

Preemergence herbicidal action

In a greenhouse, plant seeds are sown in flower pots of 12-15 cm in diameter such that 12-25 plants are able to develop in each pot. Directly after sowing, the surface of the soil is treated with an aqueous suspension of the active ingredients, obtained from a 10% wettable powder. Two different concentration series are employed, corresponding to rates of application of 2 and 1 kg of active ingredient per hectare respectively. The pots are then kept in the greenhouse at 22°-25° C. and 50-70% relative humidity. The test is evaluated after 3 weeks and the state of the plants is assessed in accordance with the following rating of the European Weed Research Council (EWRC):

9=normal growth, as untreated controls.
6-9=slight damage
5=moderate damage
2-4=severe damage
1=plant withered.

The results obtained for compounds 1-4 are as follows:

| Compound | 1 | | 2 | | 3 | | 4 | |
|---|---|---|---|---|---|---|---|---|
| rate of application kg/ha | 2 | 1 | 2 | 1 | 2 | 1 | 2 | 1 |
| Plant | | | | | | | | |
| barley | 8 | 8 | 8 | 9 | 6 | 9 | 9 | 9 |
| wheat | 8 | 8 | 8 | 9 | 6 | 8 | 8 | 9 |
| maize | 6 | 8 | 9 | 9 | 8 | 9 | 7 | 9 |
| rice | 6 | 7 | 7 | 9 | 6 | 8 | 6 | 9 |
| alopecurus myosuroides | 1 | 2 | 1 | 2 | 1 | 2 | 1 | 1 |
| digitaria sanguinalis | 1 | 1 | 1 | 1 | 1 | 1 | 1 | 1 |
| echinochloa crus galli | 1 | 1 | 1 | 2 | 1 | 3 | 1 | 1 |
| sorghum halepense | 2 | 2 | 1 | 1 | 1 | 1 | 2 | 3 |
| rottboellia exaltata | 1 | 1 | 1 | 2 | 1 | 1 | 1 | 3 |
| abutilon sp. | 1 | 1 | 1 | 2 | 1 | 1 | 1 | 2 |
| sida spinosa | 1 | 1 | 1 | 1 | 1 | 1 | 1 | 2 |
| amarantus rehoflexus | 1 | 1 | 1 | 1 | 1 | 1 | 1 | 1 |
| sinapis alba | 1 | 1 | 1 | 2 | 1 | 4 | 2 | 3 |
| solanum nigrum | 1 | 1 | 1 | 1 | 1 | 1 | 1 | 1 |
| stellaria media | 1 | 1 | 1 | 1 | 1 | 1 | 1 | 3 |
| chrysanthemum leuc. | 1 | 1 | 1 | 1 | 1 | 1 | 1 | 1 |
| galium aparine | 1 | 1 | 2 | 4 | 2 | 4 | 1 | 1 |
| viola tricolor | 1 | 1 | 1 | 1 | 1 | 1 | 1 | 1 |
| veronica sp. | 1 | 1 | 1 | 1 | 1 | 1 | 1 | 1 |

Postemergence herbicidal action

Different cultivated plants and weeds are reared from seeds in pots in a greenhouse until they have reached the 4-6 leaf stage. The plants are then sprayed with aqueous emulsions (obtained from a 25% emulsifiable concentrate) at rates of application of 2 and 1 kg/ha respectively. The treated plants are then kept under optimum conditions of light, regular watering, 22°-25° C., and 70-70% relative humidity. The test is evaluated 15 days after treatment. The state of the plants is assessed in accordance with the same rating as employed for the preemergence test. The results obtained with compounds 2 and 4 are as follows:

| Compound | 2 | | 4 | |
|---|---|---|---|---|
| rate of application kg/ha | 2 | 1 | 2 | 1 |
| Plant | | | | |
| wheat | 7 | 9 | 6 | 6 |
| alopecurus myosuroides | 3 | 4 | 3 | 3 |
| echinochloa crus galli | 2 | 3 | 1 | 1 |
| abutilon sp. | 1 | 1 | 1 | 1 |
| sida spinosa | 2 | 2 | 3 | 3 |
| amarantus retroflexus | 1 | 1 | 1 | 1 |
| chenopodium album | 1 | 1 | 1 | 1 |
| solanum nigrum | 1 | 1 | 1 | 1 |
| ipomoea purpurea | 1 | 1 | 1 | 1 |
| sinapis alba | 1 | 1 | 1 | 1 |
| stellaria media | 1 | 1 | 1 | 1 |
| chrysanthemum leucum | 1 | 1 | 1 | 1 |
| galium aparine | 1 | 1 | 1 | 1 |
| viola tricolor | 1 | 1 | 1 | 1 |
| veronica sp. | 1 | 1 | 1 | 1 |

Selective herbicidal action postemergence on rice

Twenty-five-day-old rice plants are transplanted into large rectangular asbestos cement containers in a greenhouse. Seeds of the weeds occurring in rice crops, namely Echinochloa crus galli, Cyperus difformis, Ammania and Rotala, are then sown between the rows of rice plants. The containers are well watered and kept at a temperature of about 25° C. and at high humidity. Twelve days later, when the weeds have emerged and reached the 2-3 leaf stage, the soil in each of the containers is covered with a layer of water to a height of 2.5 cm. The active ingredient is then applied in the form of an emulsifiable concentrate with a pipette between the rows of plants. The emulsifiable concentrate is diluted and applied such that it corresponds to a field application rate of 1 and ½ kg/ha respectively. The test is evaluated 4 weeks later. The results obtained with compounds 1 and 2 are as follows:

| Compound | 1 | | 2 | |
|---|---|---|---|---|
| rate of application kg/ha | 1 | ½ | 1 | ½ |
| rice | 6 | 7 | 6 | 6 |
| echinochloa crus galli | 2 | 3 | 1 | 2 |
| cyperus difformis | 4 | 4 | 1 | 2 |
| ammania indica | 1 | 1 | 1 | 1 |
| rotala indica | 1 | 4 | 2 | 3 |

Desiccation and defoliation action

Cotton plants of the variety Deltapine are reared in earthenware pots in a greenhouse. After the first capsules have formed, the plants are sprayed with aqueous compositions of the active ingredients at rates of application corresponding to 1, 2, 0.6 and 0.3 kg/ha respectively in field application. Untreated plants act as controls. Evaluation of the test is made 3, 7 and 14 days after application of the active ingredient by determining the degree of defoliation (percentage of fallen leaves) and of desiccation (drying out of the leaves remaining on the plant). Plants treated with compounds 1 to 7 at rates of application of 0.6 and 1.2 kg/ha are left after 7 days with only a few dried out leaves (higher than 80% defoliation and desiccation). Compound 3 has the best action.

What is claimed is:

1. A compound of the formula

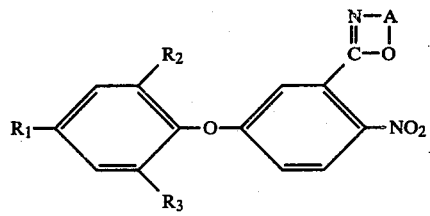

wherein A is propylene or propenylene optionally substituted by $C_1$—$C_4$ alkyl or $C_1$—$C_4$ haloalkyl, and each of $R_1$, $R_2$, and $R_3$ is hydrogen, halogen, trifluoromethyl, nitro or cyano.

2. A compound according to claim 1, wherein $R_1$ is hydrogen or halogen, $R_2$ is trifluoromethyl or halogen, $R_3$ is hydrogen or chlorine, and A is propylene optionally substituted by methyl or halomethyl.

3. 2-[2'-Nitro-5'-(2''-chloro-4''-trifluoromethylphenoxy)-phenyl]-5,6-dihydro-4H-1,3-oxazine according to claim 2.

4. 2-[2'-Nitro-5'-(2''-cyano-4''-chlorophenoxy)-phenyl]-5,6-dihydro-4H-1,3-oxazine according to claim 2.

5. A herbicidal and plant growth inhibiting composition which contains, as active component, a herbicidally or plant growth inhibiting effective amount of at least one compound according to claim 1, and an inert carrier.

6. A method of controlling undesired plant growth at a locus, which comprises applying to said locus a herbicidally effective amount of a compound according to claim 1.

7. A method of selectively controlling weeds in crops of useful plants, which comprises applying thereto a herbicidally effective amount of a compound according to claim 1.

8. A method of selectively controlling weeds in crops of cereals, rice and maize, which comprises applying thereto a herbicidally effective amount of a compound according to claim 1.

9. A method of defoliating and desiccating parts of plants above the soil, which comprises applying thereto a defoliating and desiccating effective amount of a compound according to claim 1.

* * * * *